(12) United States Patent
Tanaka et al.

(10) Patent No.: US 8,729,464 B2
(45) Date of Patent: May 20, 2014

(54) METHOD FOR DETERMINING STAGE OF CHRONIC KIDNEY DISEASE, DEVICE THEREFOR AND METHOD FOR OPERATING THE SAME

(75) Inventors: Noriaki Tanaka, Sakai (JP); Masahiro Kohno, Sendai (JP); Emiko Sato, Sendai (JP); Kouichi Fujiwara, Sakai (JP)

(73) Assignee: Noriaki Tanaka, Sakai-shi (JP)

( * ) Notice: Subject to any disclaimer, the term of this patent is extended or adjusted under 35 U.S.C. 154(b) by 0 days.

(21) Appl. No.: 13/700,795

(22) PCT Filed: May 30, 2011

(86) PCT No.: PCT/JP2011/062344
§ 371 (c)(1),
(2), (4) Date: Nov. 29, 2012

(87) PCT Pub. No.: WO2011/152339
PCT Pub. Date: Dec. 8, 2011

(65) Prior Publication Data
US 2013/0068945 A1    Mar. 21, 2013

(30) Foreign Application Priority Data

May 31, 2010    (JP) .................................. 2010-124367

(51) Int. Cl.
*H01J 49/04*    (2006.01)
(52) U.S. Cl.
CPC .................................. *H01J 49/0431* (2013.01)
USPC .......................... 250/288; 250/281; 250/282
(58) Field of Classification Search
USPC ........................................ 250/288, 281, 282
See application file for complete search history.

(56) References Cited

U.S. PATENT DOCUMENTS

2010/0210021 A1*  8/2010  Mischak .......................... 436/86
2011/0036717 A1*  2/2011  Mischak ....................... 204/451
2012/0193527 A1   8/2012  Abe

FOREIGN PATENT DOCUMENTS

| JP | 2009-121850 A1 | 6/2009 |
| JP | 2011-58863 A1 | 3/2011 |
| WO | WO 2011/027573 A1 | 3/2011 |

OTHER PUBLICATIONS

J. Metzger, et al.; "Capillary electrophoresis-mass spectrometry in urinary proteome analysis: current applications and future developments;" Analytical and Bioanalytical Chemistry; vol. 393; Issue 5; 2009; pp. 1431-1442 (12 Sheets)/Cited in International Search Report.

(Continued)

*Primary Examiner* — Kiet T Nguyen
(74) *Attorney, Agent, or Firm* — Kratz, Quintos & Hanson, LLP

(57) ABSTRACT

This invention provides a method or device for determining the stage of chronic kidney disease.
The present invention relates to a method for determining a stage of chronic kidney disease in a subject suffering from kidney disease, the method comprising the steps of:
(A-1) measuring the content of at least one marker selected from the group consisting of markers (1) to (16) in a specimen from the subject,
(B-1) determining the stage indicated by each marker by comparing the content of the at least one marker in the specimen from the subject, which has been measured in step (A-1), with a reference content range determined in each stage, and
(C-1) determining that when each marker indicates the same stage, which has been determined in step (A-1), the chronic kidney disease in the subject is in that stage.

11 Claims, 6 Drawing Sheets

(56) References Cited

OTHER PUBLICATIONS

T. Igakusha; "Clinical Practice Guidebook for Diagnosis and Treatment of Chronic Kidney Disease 2009;" Japanese Society of Nephrology; revised May 23, 2007; issued 2009; pp. 12-13, front sheet and end sheet and translation (8 Sheets total)/p. 2 of specification.

International Search Report for International Application No. PCT/JP2011/062344 dated Jul. 12, 2011.

Extended European Search Report mailed Oct. 17, 2013 in counterpart application No. 11789742.1.

Keisuke Nakayama et al: "Plasma alpha-Oxoaldehyde Levels in Diabetic and Nondiabetic Chronic Kidney Disease Patients", American Journal of Nephrology, vol. 28, Jun. 12, 2008, pp. 871-878.

Toshimitsyu Niwa: "Recent progress in the analysis of uremic toxins by mass spectrometry", Journal of Chromatography B, Biomedical Sciences & Applications, vol. 877, No. 25, Sep. 1, 2009, pp. 2600-2606.

Sascha David et al.: "Circulating angiopoietin-2 levels increase with progress of chronic kidney disease", Nephrology Dialysis Transplantation, vol. 25, No. 8, Feb. 22, 2010, pp. 2571-2576.

Ellen R. Brooks et al.: "Methylated arginine derivatives in children and adolescents with chronic kidney disease", Journal of the International Pediatric Nephrology Association, vol. 24, No. 1, Oct. 2, 2008, p. 129-134.

Lewen Jia et al.: "Metabolomic identification of potential phospholipid biomarkers for chronic glomerulonephritis by using high performance liquid chromatography-mass spectrometry", Journal of Chromatography B, Biomedical Sciences & Applications, vol. 860, No. 1, Nov. 8, 2007, pp. 134-140.

Bhaskar Malayappan et al.: "Urinary analysis of 8-oxoguanine, 8-oxoguanosine, fapy-guanine and 8-oxo-2'-deoxyguanosine by high-performance liquid chromagraphy-electrospray tandem mass spectrometry as a measure of oxidative stress", Journal of Chromatography, Science Publishers B. V, vol. 1167, No. 1, Sep. 11, 2007, pp. 54-62.

* cited by examiner

METHOD FOR DETERMINING STAGE OF CHRONIC KIDNEY DISEASE, DEVICE THEREFOR AND METHOD FOR OPERATING THE SAME

TECHNICAL FIELD

The present invention relates to a method and a device for determining a stage of chronic kidney disease, and a method for operating the device.

BACKGROUND ART

Chronic kidney disease (CKD) is a disease that progresses when a finding indicative of kidney damage or a state where deterioration of kidney function chronically continues remains untreated. As it progresses, the disease results in end-stage renal failure, and survival without artificial dialysis or kidney transplantation becomes difficult.

End-stage renal failure is increasing on a global scale. To deal with this disease, early treatment and early detection, specifically detection when the disease is so-called "hidden chronic kidney disease," are said to be important.

It is said that there are currently about 13,300,000 CKD patients in Japan. This indicates that about 1 in 8 adults is a CKD patient.

The most commonly occurring primary disease among dialysis patients is diabetic nephropathy, which is one of the three major diabetic complications. Since diabetic nephropathy is one of the CKDs, patients with diabetes are likely to get CKD. According to the National Health and Nutrition Examination Survey in 2006 (Ministry of Health, Labor and Welfare), the number of diabetic patients is estimated to be 8,200,000, and 18,700,000 including potential diabetic patients. Since it is assumed that 30 percent of these patients will develop renal failure, the number of CKD patients will continue to increase in the future. The annual medical expenses for dialysis treatment in Japan are, for example, approximately 5,400,000 yen per person, and 1.5 trillion yen as a whole. Since the number of dialysis patients is increasing, the medical expenses required for dialysis treatment are also increasing. Therefore, measures to curtail these medical expenses are urgently needed. For this reason, early detection of kidney damage, early treatment to prevent symptom aggravation, and, in the end, reduction of the number of patients introduced to dialysis as much as possible are considered globally important.

CKD is staged according to the glomerular filtration rate (GFR), which is an evaluation index of kidney function. Namely, CKD is classified into five stages, according to GFR (NPL 1).

However, the thus-performed determination of CKD staging is based on the serum creatinine concentration. Since the serum creatinine concentration is strongly affected by muscle mass, there is a problem such that performing an accurate determination excluding such an influence is difficult. Further, since an increase in the serum creatinine concentration is not observed until the estimated GFR (eGFR) becomes 50% or less, minor kidney damage is difficult to find. Despite such circumstances, appropriate determination methods in place of the aforementioned method have not been developed.

CITATION LIST

Non-Patent Literature

NPL 1: Pages 12 to 13 of *CKD Shinryo Guide* [Clinical Practice Guidebook for Diagnosis and Treatment of Chronic Kidney Disease] revised on May 23, 2007, edited by the Japanese Society of Nephrology, issued in 2009.

SUMMARY OF INVENTION

Technical Problem

An object of the present invention is to provide a method and a device for determining a stage of chronic kidney disease, and a method for operating the device.

Solution to Problem

With constant trial and error, the present inventor made accurate comparisons of pre-dialysis plasma and pre-dialysis urine of CKD patients between stages, and, with great effort, searched for a low molecular compound whose content is considered to have a relation with stage progression.

Through such prolonged effort, the present inventors finally found the presence of a low molecular compound whose content is increased with stage progression. Further, the present inventors found the presence of a low molecular compound that is observed only in a particular stage. Moreover, as a result of extensive research, the present inventor found that the content of such a specific low molecular compound in plasma can be used as an index in appropriate determination of a stage of chronic kidney disease.

Specifically, the present inventions are as follows:

(I) Method for Determining the Stage of Chronic Kidney Disease

[I-1]
A method for determining a stage of chronic kidney disease in a subject suffering from kidney disease, the method comprising the steps of:

(A-1) measuring the content of at least one marker selected from the group consisting of markers (1) to (16) shown below by subjecting a specimen from the subject using liquid chromatography/time of flight mass spectrometry under specific conditions indicated below, and (B-1) determining the stage indicated by each marker by comparing the content of each marker in the specimen from the subject, which has been measured in step (A-1), with a reference content range determined in each stage:

Liquid-Chromatography Conditions
Liquid-chromatography equipment: Agilent 1100 Series (Agilent);
Column: Cadenza C18 2×150 mm, 3 μm (Imtakt);
Pre-column: TCI OPTI-GUARD Fit ODS (TCI);
Mobile phase A: 0.05% formic acid;
Mobile phase B: acetonitrile;
For gradient elution:
0 to 15 min: linear gradient from 5% to 95% mobile phase B in mobile phase A,
15 to 20 min: linear gradient from 95% to 100% mobile phase B in mobile phase A, and
20 to 35 min: 100% mobile phase B is kept;
Flow rate: 0.2 mL/min; and
Measurement sample content: 5 μL.
Time of Flight Mass Spectrometry Conditions
Measuring range: m/z 70 to 1,000;
Orifice 1 voltage: 10 to 40V, −10 to (−40) V sweep;
Ion guide voltage: 500 to 2,500 V sweep;
Detector: 2,800 V; and
Measuring equipment: Accu TOF JMS-T100LC (JEOL).
Markers Marker (1): marker having a retention time of 2.03±0.5 (min) and an accurate mass (m/z) of 104.10±10 mDa in positive ion measurement $[M+H]^+$;

Marker (2): marker having a retention time of 3.80±0.5 (min) and an accurate mass (m/z) of 257.10±10 mDa in positive ion measurement $[M+H]^+$;

Marker (3): marker having a retention time of 6.52±0.5 (min) and an accurate mass (m/z) of 312.12±10 mDa in positive ion measurement $[M+H]^+$;

Marker (4): marker having a retention time of 6.87±0.5 (min) and an accurate mass (m/z) of 232.15±10 mDa in positive ion measurement $[M+H]^+$;

Marker (5): marker having a retention time of 8.32±0.5 (min) and an accurate mass (m/z) of 265.12±10 mDa in positive ion measurement $[M+H]^+$;

Marker (6): marker having a retention time of 10.54±0.5 (min) and an accurate mass (m/z) of 300.22±10 mDa in positive ion measurement $[M+H]^+$;

Marker (7): marker having a retention time of 6.57±0.5 (min) and an accurate mass (m/z) of 211.08±10 mDa in negative ion measurement $[M-H]^-$;

Marker (8): marker having a retention time of 7.19±0.5 (min) and an accurate mass (m/z) of 411.13±10 mDa in negative ion measurement $[M-H]^-$;

Marker (9): marker having a retention time of 8.25±0.5 (min) and an accurate mass (m/z) of 263.10±10 mDa in negative ion measurement $[M-H]^-$;

Marker (10): marker having a retention time of 2.26±0.5 (min) and an accurate mass (m/z) of 286.13±10 mDa in positive ion measurement $[M+H]^+$;

Marker (11): marker having a retention time of 8.29±0.5 (min) and an accurate mass (m/z) of 495.23±10 mDa in positive ion measurement $[M+H]^+$;

Marker (12): marker having a retention time of 8.32±0.5 (min) and an accurate mass (m/z) of 529.22±10 mDa in positive ion measurement $[M+H]^+$;

Marker (13): marker having a retention time of 8.64±0.5 (min) and an accurate mass (m/z) of 304.13±10 mDa in positive ion measurement $[M+H]^+$;

Marker (14): marker having a retention time of 9.24±0.5 (min) and an accurate mass (m/z) of 389.21±10 mDa in positive ion measurement $[M+H]^+$;

Marker (15): marker having a retention time of 3.93±0.5 (min) and an accurate mass (m/z) of 197.05±10 mDa in negative ion measurement $[M-H]^-$; and Marker (16): marker having a retention time of 5.55±0.5 (min) and an accurate mass (m/z) of 327.09±10 mDa in negative ion measurement $[M-H]^-$.

Hereinbelow, the conditions of the liquid chromatography and the time of flight mass spectrometry are the same as above, and markers (1) to (16) are those specified by the aforementioned retention time and accurate mass, unless otherwise specified.

[I-2]

The method according to Item I-1, further comprising the step of: (C-1) determining that when each marker indicates the same stage, which has been determined in step (B-1), the chronic kidney disease in the subject is in that stage.

[I-3]

The method according to Item I-1 or Item I-2, wherein the marker measured in step (A-1) is at least one marker selected from the group consisting of markers (1) to (9).

[I-4]

A method for determining a stage of chronic kidney disease in a subject suffering from kidney disease, comprising the steps of:

(A-2) measuring at least one marker selected from the group consisting of markers (10) to (16) shown above by subjecting a specimen from the subject using liquid chromatography/time of flight mass spectrometry under the aforementioned specific conditions, and (B-2) determining that the stage of chronic kidney disease in the subject is severe when the at least one marker is detected in step (A-2).

[I-5]

A method for determining a stage of chronic kidney disease in a subject suffering from kidney disease, comprising the steps of:

(B-1) determining the stage indicated by each marker by comparing the content of at least one marker selected from the group consisting of markers (1) to (16) shown above in a specimen from the subject, the content of the at least one marker having been measured by liquid chromatography/time of flight mass spectrometry under the aforementioned specific conditions, with a reference content range determined in each stage; and (C-1) determining that when each marker indicates the same stage, which has been determined in step (B-1), the chronic kidney disease in the subject is in that stage.

[I-6]

The method according to Item I-5, wherein the marker of interest in step (B-1) is at least one marker selected from the group consisting of markers (1) to (9).

(II) Device for Determining the Stage of Chronic Kidney Disease and Method for Operating the Device

[II-1]

A device for determining a stage of chronic kidney disease in a subject suffering from kidney disease, the device comprising:

(A-1) a means of measuring the content of at least one marker selected from the group consisting of markers (1) to (16) shown above in a specimen from the subject using liquid chromatography/time of flight mass spectrometry under the aforementioned specific conditions, (B-1) a means of determining the stage indicated by each marker by comparing the content of each marker in the specimen from the subject, which has been measured by means (A-1), with a reference content range determined in each stage, and (C-1) a means of determining that when each marker indicates the same stage, which has been determined by means (B-1), the chronic kidney disease in the subject is in that stage.

The device according to Item II-1, wherein the marker measured by means (A-1) is at least one marker selected from the group consisting of markers (1) to (9).

[II-3]

A device for determining a stage of chronic kidney disease in a subject suffering from kidney disease, the device comprising:

(A-2) a means of measuring at least one marker selected from the group consisting of markers (10) to (16) shown above using liquid chromatography/time of flight mass spectrometry under the aforementioned specific conditions, and (B-2) a means of determining that the stage of chronic kidney disease in the subject is severe when the at least one marker is detected by means (A-2).

[II-4]

A method for operating the device of Item II-1, the method comprising the steps of:

(a-1) operating means (A-1) to measure the content of at least one marker selected from the group consisting of markers (1) to (16) in a specimen extracted from a subject, (b-1) operating means (B-1) to determine a stage indicated by each marker by comparing the content measured in step (a-1) with a reference content range determined in each stage, and (c-1) operating means (C-1) to determine that when each marker indicates the same stage, which has been determined in step (b-1), the chronic kidney disease in the subject is in that stage.

[II-5]

A method for operating the device of Item II-2, comprising the steps of:

(a-1) operating means (A-1) to measure the content of at least one marker selected from the group consisting of markers (1) to (9) in a specimen extracted from a subject, (b-1) operating means (B-1) to determine a stage indicated by each marker by comparing the content measured in step (a-1) with a reference content range determined in each stage, and (c-1) operating means (C-1) to determine that when each marker indicates the same stage, which has been determined in step (b-1), the chronic kidney disease in the subject is in that stage.

[II-6]

A method for operating the device of Item II-3, comprising the steps of:

(a-2) operating means (A-2) to measure at least one marker selected from the group consisting of markers (10) to (16) in a specimen extracted from a subject, and (b-2) operating means (B-2) to determine that a stage of chronic kidney disease in the subject is severe when the at least one marker is detected in the specimen in step (a-2).

(III) Kit for Determining the Stage of Chronic Kidney Disease

[III-1]

A kit for determining a stage of chronic kidney disease comprising a material required for detecting at least one marker selected from the group consisting of markers (1) to (16) shown above using liquid chromatography/time of flight mass spectrometry under the aforementioned specific conditions.

[III-2]

A kit for determining a stage of chronic kidney disease comprising a material required for detecting at least one marker selected from the group consisting of markers (1) to (9) shown above using liquid chromatography/time of flight mass spectrometry under the aforementioned specific conditions.

[III-3]

A kit for determining a stage of chronic kidney disease comprising a material required for detecting at least one marker selected from the group consisting of markers (10) to (16) shown above using liquid chromatography/time of flight mass spectrometry under the aforementioned specific conditions.

Advantageous Effects of Invention

According to the present invention, the use of novel markers ensures more appropriate determination of chronic kidney disease stage than the use of conventional methods.

In particular, according to the present invention, the stage of chronic kidney disease can be easily determined at low cost and in a short time.

Further, by determining the stage of chronic kidney disease using the present invention, many patients with kidney disease, as well as medical institutions involving diagnosis, treatment, etc., of kidney disease are expected to enjoy many advantages.

DESCRIPTION OF EMBODIMENTS

Figure 1:
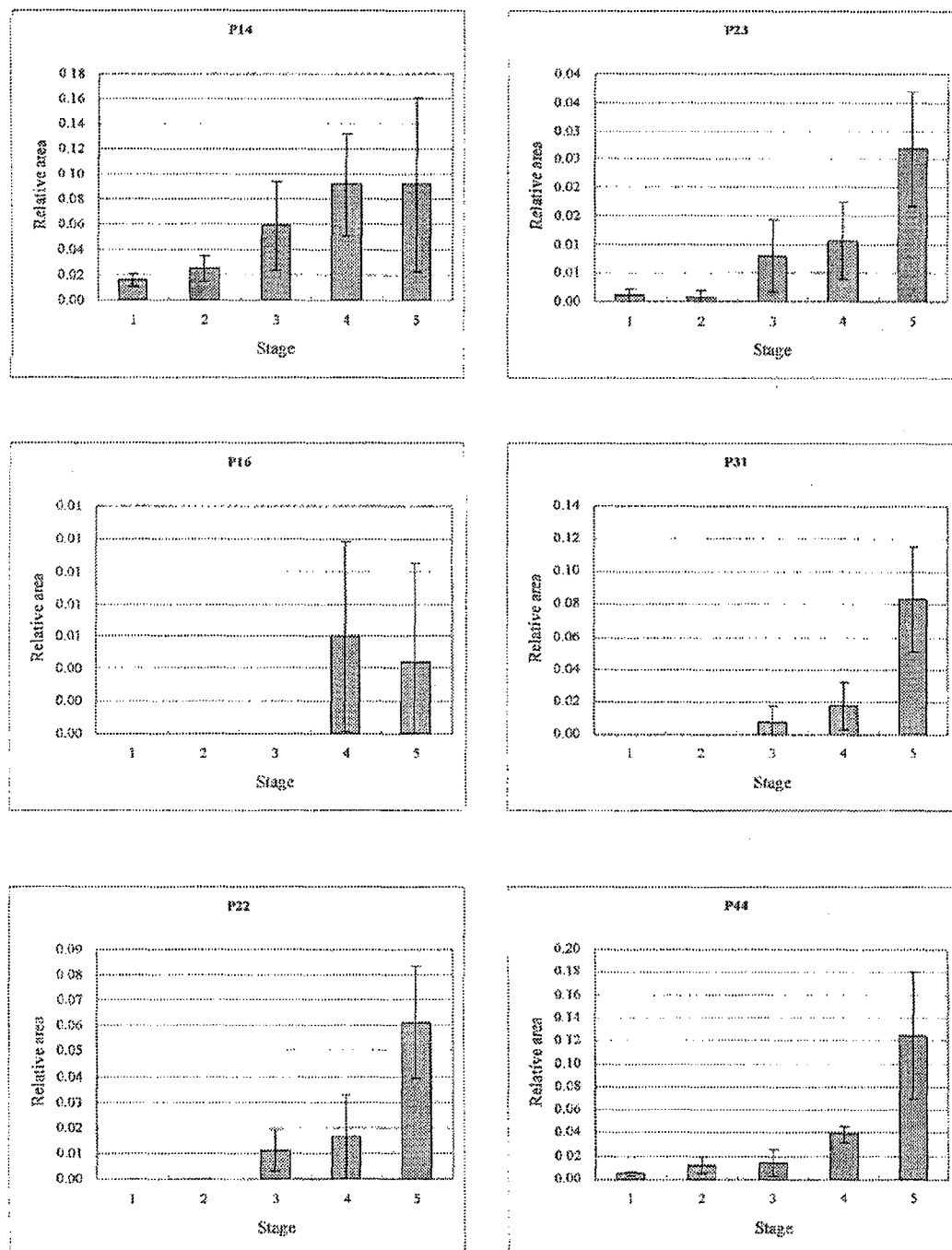
FIG. 1 shows graphs demonstrating the component change (SN>20) of each marker (ESI-Positive) in each stage.

I. Method for Determining the Stage of Chronic Kidney Disease

The first embodiment (method (1)) of determining the stage of chronic kidney disease according to the present invention includes the steps of:

(A-1) evaluating the content of at least one marker in a specimen from a subject, the at least one marker being selected from the group consisting of markers (1) to (16) wherein the retaining time and the accurate mass (m/z) are as defined below in the measurement of liquid chromatography/time of flight mass spectrometry performed under the following conditions:

Liquid-Chromatography Conditions

Liquid-chromatography equipment: Agilent 1100 Series (Agilent);

Column: Cadenza C18 2×150 mm, 3 μm (Imtakt);

Pre-column: TCI OPTI-GUARD Fit ODS (TCI);

Mobile phase A: 0.05% formic acid;

Mobile phase B: acetonitrile;

For gradient elution:

0 to 15 min: linear gradient from 5% to 95% mobile phase B in mobile phase A, 15 to 20 min: linear gradient from 95% to 100% mobile phase B in mobile phase A, and 20 to 35 min: 100% mobile phase B is kept;

Flow rate: 0.2 mL/min; and

Measurement sample content: 5 μL.

Time of Flight Mass Spectrometry Conditions

Measuring range: m/z 70 to 1,000;

Orifice 1 voltage: 10 to 40V, −10 to (−40) V sweep;

Ion guide voltage: 500 to 2,500 V sweep;

Detector: 2,800 V; and

Measuring equipment: Accu TOF JMS-T100LC (JEOL).

(1): marker having a retention time of 2.03±0.5 (min) and an accurate mass (m/z) of 104.10±10 mDa in positive ion measurement $[M+H]^+$;

(2): marker having a retention time of 3.80±0.5 (min) and an accurate mass (m/z) of 257.10±10 mDa in positive ion measurement $[M+H]^+$;

(3): marker having a retention time of 6.52±0.5 (min) and an accurate mass (m/z) of 312.12±10 mDa in positive ion measurement [M+H]⁺;

(4): marker having a retention time of 6.87±0.5 (min) and an accurate mass (m/z) of 232.15±10 mDa in positive ion measurement [M+H]⁺;

(5): marker having a retention time of 8.32±0.5 (min) and an accurate mass (m/z) of 265.12±10 mDa in positive ion measurement [M+H]⁺;

(6): marker having a retention time of 10.54±0.5 (min) and an accurate mass (m/z) of 300.22±10 mDa in positive ion measurement [M+H]⁺;

(7): marker having a retention time of 6.57±0.5 (min) and an accurate mass (m/z) of 211.10±10 mDa in negative ion measurement [M−H]⁻;

(8): marker having a retention time of 7.19±0.5 (min) and an accurate mass (m/z) of 411.13±10 mDa in negative ion measurement [M−H]⁻;

(9): marker having a retention time of 8.25±0.5 (min) and an accurate mass (m/z) of 263.10±10 mDa in negative ion measurement [M−H]⁻;

(10): marker having a retention time of 2.26±0.5 (min) and an accurate mass (m/z) of 286.13±10 mDa in positive ion measurement [M+H]⁺;

(11): marker having a retention time of 8.29±0.5 (min) and an accurate mass (m/z) of 495.23±10 mDa in positive ion measurement [M+H]+;

(12): marker having a retention time of 8.32±0.5 (min) and an accurate mass (m/z) of 529.22±10 mDa in positive ion measurement [M+H]⁺;

(13): marker having a retention time of 8.64±0.5 (min) and an accurate mass (m/z) of 304.13±10 mDa in positive ion measurement [M+H]⁺;

(14): marker having a retention time of 9.24±0.5 (min) and an accurate mass (m/z) of 389.21±10 mDa in positive ion measurement [M+H]⁺;

(15): marker having a retention time of 3.93±0.5 (min) and an accurate mass (m/z) of 197.05±10 mDa in negative ion measurement [M−H]⁻; and (16): marker having a retention time of 5.55±0.5 (min) and an accurate mass (m/z) of 327.09±10 mDa in negative ion measurement [M−H]⁻;

(B-1) determining the stage indicated by each marker by comparing the content of each marker in the specimen from the subject, which has been measured in step (A-1), with a reference content range determined in each stage, and (C-1) determining that when each marker indicates the same stage, which has been determined in step (B-1), the chronic kidney disease in the subject is in that stage.

The second embodiment (method (2)) of determining the stage of chronic kidney disease according to the present invention includes the steps of:

(A-2) evaluating the content of at least one marker in a specimen from a subject, the at least one marker being selected from the group consisting of markers (10) to (16) wherein the retaining time and the accurate mass (m/z) are as shown below in the measurement of liquid chromatography/time of flight mass spectrometry performed under the following conditions:

Liquid Chromatography Conditions
Liquid-chromatography equipment: Agilent 1100 Series (Agilent);
Column: Cadenza C18 2×150 mm, 3 µm (Imtakt);
Pre-column: TCI OPTI-GUARD Fit ODS (TCI);
Mobile phase A: 0.05% formic acid;
Mobile phase B: acetonitrile;
For gradient elution:
0 to 15 min: linear gradient from 5% to 95% mobile phase B in mobile phase A,
15 to 20 min: linear gradient from 95% to 100% mobile phase B in mobile phase A, and
20 to 35 min: 100% mobile phase B is kept;
Flow rate: 0.2 mL/min; and
Measurement sample content: 5 µL.

Time of Flight Mass Spectrometry Conditions
Measuring range: m/z 70 to 1,000;
Orifice 1 voltage: 10 to 40V, −10 to (−40) V sweep;
Ion guide voltage: 500 to 2,500 V sweep;
Detector: 2,800 V; and
Measuring equipment: Accu TOF JMS-T100LC (JEOL).

(10): marker having a retention time of 2.26±0.5 (min) and an accurate mass (m/z) of 286.13±10 mDa in positive ion measurement [M+H]⁺;

(11): marker having a retention time of 8.29±0.5 (min) and an accurate mass (m/z) of 495.23±10 mDa in positive ion measurement [M+H]⁺;

(12): marker having a retention time of 8.32±0.5 (min) and an accurate mass (m/z) of 529.22±10 mDa in positive ion measurement [M+H]⁺;

(13): marker having a retention time of 8.64±0.5 (min) and an accurate mass (m/z) of 304.13±10 mDa in positive ion measurement [M+H]⁺;

(14): marker having a retention time of 9.24±0.5 (min) and an accurate mass (m/z) of 389.21±10 mDa in positive ion measurement [M+H]⁺;

(15): marker having a retention time of 3.93±0.5 (min) and an accurate mass (m/z) of 197.06±10 mDa in negative ion measurement [M−H]⁻; and (16): marker having a retention time of 5.55±0.5 (min) and an accurate mass (m/z) of 327.09±10 mDa in negative ion measurement [M−H]⁻; and (B-2) determining that the stage of chronic kidney disease in the subject is severe when the presence of the at least one marker is confirmed in step (A-2).

The methods (1) and (2) for determining the stage of chronic kidney disease according to the present invention are methods in which specimens from subjects are examined to determine to what stage each of the subjects belongs.

As to the stage, for example, staging based on the glomerular filtration rate (GFR), which is an evaluation index of kidney function, can be used. Specifically, as shown in Table 1, five stages according to the amount of GFR can be used without modification (pages 12 to 13 of the *CRD Shinryo Guide* [Clinical Practice Guidebook for Diagnosis and Treatment of Chronic Kidney Disease] revised on May 23, 2007, edited by the Japanese Society of Nephrology, issued in 2009). The amount of GFR can be estimated from an estimation equation in which the serum creatinine level is based. The amount of this estimated GFR is referred to as "eGFR."

TABLE 1

| Stage | Explanation of Severity | Amount of GFR (mL/min/1.73 m²) |
|---|---|---|
| 1 | Normal or increased GFR with kidney damage | ≥90 |
| 2 | Mild reduction in GFR with kidney damage | 60-89 |

TABLE 1-continued

| Stage | Explanation of Severity | Amount of GFR (mL/min/1.73 m$^2$) |
|---|---|---|
| 3 | Moderate reduction in GFR | 30-59 |
| 4 | Severe reduction in GFR | 15-29 |
| 5 | Renal failure | <15 |

For patients who are not under treatment for dialysis, the necessity of introduction of dialysis treatment may be determined based on the stage determined by method (1) or (2), i.e., the method for determining the stage of chronic kidney disease of the present invention. Specifically, when the disease is in an advanced stage, introduction of dialysis treatment may be considered necessary; and when the disease is in a low stage, introduction of dialysis treatment may be considered unnecessary.

For example, when the stage of disease in the staging (Table 1) in which the glomerular filtration rate (GFR), which is an evaluation index of kidney function is based, is rated 4 (severe reduction in GFR) or 5 (renal failure), introduction of dialysis treatment may be considered necessary; and when the stage of disease is rated 1, 2, or 3, introduction of dialysis treatment may be considered unnecessary.

The method for determining the stage of chronic kidney disease according to the present invention includes the step (step (A-1) or step (A-2)) of evaluating the marker content, and the step ((B-1) and (C-1), or (B-2)) of determining the stage of chronic kidney disease. Hereinbelow, each step of the present invention is detailed.

Step of Evaluating the Marker Content

The step of evaluating the marker content is a step of evaluating the content of at least one marker selected from the group consisting of (1) to (16) or (10) to (16) in a specimen extracted from a human.

There is no particular limitation on the specimens, and blood-derived specimens, urine specimens, and the like can be used as the specimens. As the blood-derived specimens, whole blood, serum, or plasma can be used. Of these, serum and plasma are preferable. To reduce the separation time or prevent the dissolution of an evaluation target marker, plasma is more preferable. Additionally, to prevent the dissolution of the evaluation target marker, a substance exhibiting an anticoagulant effect by a chelated effect can be added to such blood-derived specimens. Examples of the material exhibiting an anticoagulant activity include EDTA (Ethylene Diamine-Tetraacetic Acid), and the like. Likewise, for the same purpose, material exhibiting a protease inhibitory activity can be added. Examples of the material exhibiting an anticoagulant activity include aprotinin, and the like.

When the specimen is stored in a frozen state after extraction, it may be subjected beforehand to a pretreatment step, as necessary, and then subjected to a means of evaluating the marker content. An example of the pretreatment step is a step of removing an undesired substance by centrifugation, etc. For example, when plasma is used as a blood-derived specimen, it may be subjected to the means after removal of precipitate by centrifugation. Preferable examples of the conditions for centrifugation include 3,000 to 10,000 g for 5 to 10 minutes, and more preferably 10,000 g and 10 minutes. As the pretreatment step, a solid phase extraction step may be performed, if necessary. For example, a step using a hydrophobic adsorbent can be used. In this case, solid phase extraction may be performed by using a hydrophobic adsorbent as a solid phase extraction column. As the solid phase extraction column, which is a hydrophobic adsorbent, a Sep-Pak Light Cartridge C18 column (Japanese Waters, Inc.) can be used. In this case, for example, elution can be performed using 90% methanol.

There is no limitation on the step of evaluating the content of the at least one marker selected from the group consisting of (1) to (16) or (10) to (16), as long as the step can confirm the presence or absence of the marker(s), or the step can perform quantitative measurement.

By adjusting the detection limit of the evaluation means to not less than the reference content of a certain marker, whether the marker is present in a specimen in an amount exceeding the reference content can be evaluated using the evaluation means. In this case, as a step of confirming the presence or absence of the marker, a step in which a marker is considered absent when the content is not more than the detection limit of the evaluation means, and a marker is considered present when the content is not less than the detection limit, can be used.

In the step of quantitative measurement, for example, a liquid chromatography-time of flight mass spectrometer (LC-TOF MS), liquid chromatography-quadrupole mass spectrometer (LC-Q MS), high-performance liquid chromatography (HPLC), spectrophotometer, chemiluminescence measuring instrument, etc., can be used. From the viewpoint of reproducibility or measurement accuracy, LC-TOF MS is preferable.

For example, when LC-TOF MS is used in the evaluation step, two or more kinds of internal standard substances are added to a specimen beforehand, and then analysis using LC-TOF MS is performed. The value obtained by dividing the m/z peak area of a marker by the average of the m/z peak areas of the internal standard substances is determined as a relative area (hereinbelow, referred to as "m/z peak relative area"), and the m/z peak relative areas of the different specimens are compared to evaluate the marker content.

Examples of the internal standard substances include benzyloxycarbonyl-L-tyrosyl-glutamic acid (Z-Tyr-Glu), tosyl-L-arginine methyl ester monohydrochloride (Tos-Arg-OMe-HCl), and the like.

The column used for liquid chromatography is not particularly limited, as long as a marker can be analyzed. Reversed-phase columns and normal-phase columns can be used; and reversed-phase columns are preferable. The filler is not limited, as long as a marker can be analyzed. Examples of the filler include C18 (octadecyl). The particle system and the length can be suitably determined.

When a more rapid or simpler determination is desired, it is preferable to evaluate the content of at least one marker selected from the group consisting of (1) to (16) or (10) to (16). When a more accurate determination is desired, it is preferable to evaluate the contents of at least two markers selected from the aforementioned group. According to the degree of desired accuracy, the contents of three markers may be evaluated, and the contents of four markers may be evaluated.

GFR has been conventionally used as an index of severity of CKD; however, since GFR is calculated based on the serum creatinine concentration, and the serum creatinine concentration is strongly affected by the muscle mass, it is difficult to remove such influence and perform accurate determination. Further, since an increase in the serum creatinine concentration cannot be acknowledged until the value of eGFR becomes 50% or less, minor kidney damage has been difficult to find. On the other hand, none of markers (1) to (16) have been used as markers. By using them as the markers, the stage of chronic kidney disease can be more appropriately determined. In particular, since the contents of markers (1) to (9) tend to increase in less severe stages, less severe kidney damage can be found by the use of these markers.

Step of Determining the Stage of Chronic Kidney Disease

The step of determining the stage of chronic kidney disease in method (1) is a step in which the marker content evaluated in step (A-1) is compared with the reference content range determined in each stage; when each marker content is within the reference content range of the same stage, the chronic kidney disease in the subject is considered to be in that stage.

The step of determining the stage of chronic kidney disease in method (2) is a step in which the stage of chronic kidney disease in the subject is considered severe when the presence of at least one marker is acknowledged in step (A-2).

The staging is not limited. For example, the staging shown in Table 1 can be used. Alternatively, staging that is generally acknowledged in this field can also be used.

The reference content range of a specific marker in a specific stage cannot be particularly limited; however, it can be determined based on the average or distribution of the marker content in specimens extracted from patients belonging to that specific stage.

It is also possible to set a reference stage, and determine a ratio relative to the marker content in the reference stage as the reference content range. For example, when the GFR-based staging is used, a stage (stages 2 to 5) can be determined according to a ratio relative to the average content in a healthy person. The reference content range in this case is specially referred to as a "standard concentration range in each stage."

Embodiments of the standard concentration range in each stage of each marker are shown below. The standard concentration range in each stage is a value obtained based on specimens extracted from five Japanese patients belonging to one stage each. However, in actually performing the determination method of the present invention, the reference content range may be newly determined in a suitable manner according to the purposes, targets, and the like.

The standard concentration range in each stage of marker (1) (the retention time is 2.03±0.5 (min) and the accurate mass (m/z) is 104.10±10 mDa in positive ion measurement [M+H]$^+$) of a patient in stage 2 to marker (1) of a healthy person is 1.5 to 3.5, 3.5 to 5.5 in stage 3, and 5.5 or more in stage 4.

The standard concentration range in each stage of marker (2) (the retention time is 3.80±0.5 (min) and the accurate mass (m/z) is 257.10±10 mDa in positive ion measurement [M+H]$^+$) of a patient in stage 3 to marker (2) of a healthy person is 7 to 9.5, 9.5 to 24 in stage 4, and 24 or more in stage 5.

The standard concentration range in each stage of marker (3) (the retention time is 6.52±0.5 (min) and the accurate mass (m/z) is 312.12±10 mDa in positive ion measurement [M+H]$^+$) of a patient in stage 2 to marker (3) of a healthy person is 2 to 2.5, 2.5 to 7 in stage 3, 7 to 24 in stage 4, and 24 or more in stage 5.

The standard concentration range in each stage of marker (4) (the retention time is 6.87±0.5 (min) and the accurate mass (m/z) is 232.15±10 mDa in positive ion measurement [M+H]$^+$) of a patient in stage 2 to marker (4) of a healthy person is 1.3 to 3, 3 to 4.5 in stage 3, 4.5 to 8 in stage 4, and 8 or more in stage 5.

The standard concentration range in each stage of marker (5) (the retention time is 8.32±0.5 (min) and the accurate mass (m/z) is 265.12±10 mDa in positive ion measurement [M+H]$^+$) of a patient in stage 3 to marker (5) of a healthy person is 1.5 to 15, 15 to 24 in stage 4, and 24 or more in stage 5.

The standard concentration range in each stage of marker (6) (the retention time is 10.54±0.5 (min) and the accurate mass (m/z) is 300.22±10 mDa in positive ion measurement [M+H]$^+$) of a patient in stage 2 to marker (6) of a healthy person is 1.5 to 6.5, 6.5 to 11 in stage 4, and 11 or more in stage 5.

The standard concentration range in each stage of marker (7) (the retention time is 6.57±0.5 (min) and the accurate mass (m/z) is 211.08±10 mDa in negative ion measurement [M−H]$^-$) of a patient in stage 2 to marker (7) of a healthy person is 3 to 5, 5 to 10 in stage 3, and 10 or more in stage 4.

The standard concentration range in each stage of marker (8) (the retention time is 7.19±0.5 (min) and the accurate mass (m/z) is 411.13±10 mDa in negative ion measurement [M−H]$^-$) of a patient in stage 3 to marker (8) of a healthy person is 1.5 to 4, 4 to 15 in stage 4, and 15 or more in stage 5.

The standard concentration range in each stage of marker (9). (the retention time is 8.25±0.5 (min) and the accurate mass (m/z) is 263.10±10 mDa in negative ion measurement [M−H]$^-$) of a patient in stage 3 to marker (9) of a healthy person is 2 to 7, 7 to 18 in stage 4, and 18 or more in stage 5.

As explained above, since the contents of markers (1) to (9) tend to increase in a less severe stage, in the case where these markers are used, the step of determining the stage of chronic kidney disease in method (1) may be a step in which each of the marker contents evaluated in step (A-1) is compared with the content of a healthy person; and, when all of the marker contents are larger than the contents of the healthy person, the subject is considered to have chronic kidney disease in at least an early stage. This step allows for early detection of chronic kidney disease, which conventionally cannot be found. The "early stage" herein is, for example, stage 1 (normal or increased GFR with kidney damage), stage 2 (mild reduction in GFR with kidney damage), and stage 3 (moderate reduction in GFR) in the staging (Table 1) in which the glomerular filtration rate (GFR), which is an evaluation index of kidney function, is based. Further, the "early stage" used herein is preferably stage 1 and stage 2, and more preferably stage 1.

As to what degree of the marker content relative to the marker content of a healthy person is considered to be in "the early stage," the degree can be suitably determined because it varies depending on the marker used, definition of the early stage, subject's attributes, and the like. The criterion may be, for example, 1.3 times, 1.4 times, 1.5 times, 2 times, 2.5 times, 3 times, 3.5 times, 4 times, 5.5 times, 6 times, 6.5 times, 7 times, 7.5 times, 8 times, 8.5 times, 9 times, 9.5 times, 10 times, and the like.

The "step that determines that the stage of chronic kidney disease is severe" in method (2) may be a step in which the disease stage in staging (Table 1) according to the glomerular filtration rate (GFR), which is the evaluation index of kidney function, is 4 (severe reduction in GFR) or 5 (renal failure).

II. Device for Determining the Stage of Chronic Kidney Disease and Method for Operating the Device The first device (device 1) for determining the stage of chronic kidney disease according to the present invention includes (A-1) a means of evaluating the content of at least one marker in a specimen extracted from a subject, the at least one marker being selected from the group consisting of markers (1) to (16) wherein the retaining time and the accurate mass (m/z) are as shown below in the measurement of liquid chromatography/time of flight mass spectrometry performed under the following conditions:
  Liquid-Chromatography Conditions
  Liquid-chromatography equipment: Agilent 1100 Series (Agilent);
  Column: Cadenza C18 2×150 mm, 3 μm (Imtakt);
  Pre-column: TCI OPTI-GUARD Fit ODS (TCI);
  Mobile phase A: 0.05% formic acid;
  Mobile phase B: acetonitrile;
  For gradient elution:
  0 to 15 min: linear gradient from 5% to 95% mobile phase B in mobile phase A,
  15 to 20 min: linear gradient from 95% to 100% mobile phase B in mobile phase A, and
  20 to 35 min: 100% mobile phase B is kept;
  Flow rate: 0.2 mL/min; and
  Measurement sample content: 5 μL.
  Time of Flight Mass Spectrometry Conditions
  Measuring range: m/z 70 to 1,000;
  Orifice 1 voltage: 10 to 40V, −10 to (−40) V sweep;
  Ion guide voltage: 500 to 2,500 V sweep;
  Detector: 2,800 V; and
  Measuring equipment: Accu TOF JMS-T100LC (JEOL).
  (1): marker having a retention time of 2.03±0.5 (min) and an accurate mass (m/z) of 104.10±10 mDa in positive ion measurement $[M+H]^+$;
  (2): marker having a retention time of 3.80±0.5 (min) and an accurate mass (m/z) of 257.10±10 mDa in positive ion measurement $[M+H]^+$;
  (3): marker having a retention time of 6.52±0.5 (min) and an accurate mass (m/z) of 312.12±10 mDa in positive ion measurement $[M+H]^+$;
  (4): marker having a retention time of 6.87±0.5 (min) and an accurate mass (m/z) of 232.15±10 mDa in positive ion measurement $[M+H]^+$;
  (5): marker having a retention time of 8.32±0.5 (min) and an accurate mass (m/z) of 265.12±10 mDa in positive ion measurement $[M+H]^+$;
  (6): marker having a retention time of 10.54±0.5 (min) and an accurate mass (m/z) of 300.22±10 mDa in positive ion measurement $[M+H]^+$;
  (7): marker having a retention time of 6.57±0.5 (min) and an accurate mass (m/z) of 211.10±10 mDa in negative ion measurement $[M-H]^-$;
  (8): marker having a retention time of 7.19±0.5 (min) and an accurate mass (m/z) of 411.13±10 mDa in negative ion measurement $[M-H]^-$;
  (9): marker having a retention time of 8.25±0.5 (min) and an accurate mass (m/z) of 263.10±10 mDa in negative ion measurement $[M-H]^-$;
  (10): marker having a retention time of 2.26±0.5 (min) and an accurate mass (m/z) of 286.13±10 mDa in positive ion measurement $[M+H]^+$;
  (11): marker having a retention time of 8.29±0.5 (min) and an accurate mass (m/z) of 495.23±10 mDa in positive ion measurement $[M+H]^+$;
  (12): marker having a retention time of 8.32±0.5 (min) and an accurate mass (m/z) of 529.22±10 mDa in positive ion measurement $[M+H]^+$;
  (13): marker having a retention time of 8.64±0.5 (min) and an accurate mass (m/z) of 304.13±10 mDa in positive ion measurement $[M+H]^+$;
  (14): marker having a retention time of 9.24±0.5 (min) and an accurate mass (m/z) of 389.21±10 mDa in positive ion measurement $[M+H]^+$;
  (15): marker having a retention time of 3.93±0.5 (min) and an accurate mass (m/z) of 197.06±10 mDa in negative ion measurement $[M-H]^-$; and
  (16): marker having a retention time of 5.55±0.5 (min) and an accurate mass (m/z) of 327.09±10 mDa in negative ion measurement $[M-H]^-$;

(B-1) a means of determining the stage indicated by each marker by comparing the content of each marker in the specimen from the subject, which has been measured by means (A-1), with a reference content range determined in each stage, and (C-1) a means of determining that when each marker indicates the same stage, which has been determined by means (B-1), the chronic kidney disease in the subject is in that stage.

The second device (device (2)) for determining the stage of chronic kidney disease according to the present invention includes (A-2) a means of evaluating the content of at least one marker in a specimen extracted from a human, the at least one marker being selected from the group consisting of markers (10) to (16) wherein the retaining time and the accurate mass (m/z) are as shown below in the measurement of liquid chromatography/time of flight mass spectrometry performed under the following conditions:
  Liquid Chromatography Conditions
  Liquid-chromatography equipment: Agilent 1100 Series (Agilent);
  Column: Cadenza C18 2×150 mm, 3 μm (Imtakt);
  Pre-column: TCI OPTI-GUARD Fit ODS (TCI);
  Mobile phase A: 0.05% formic acid;
  Mobile phase B: acetonitrile;
  For gradient elution:
  0 to 15 min: linear gradient from 5% to 95% mobile phase B in mobile phase A,
  15 to 20 min: linear gradient from 95% to 100% mobile phase B in mobile phase A, and
  20 to 35 min: 100% mobile phase B is kept;
  Flow rate: 0.2 mL/min; and
  Measurement sample content: 5 μL.
  Time of Flight Mass Spectrometry Conditions
  Measuring range: m/z 70 to 1,000;
  Orifice 1 voltage: 10 to 40V, −10 to (−40) V sweep;
  Ion guide voltage: 500 to 2,500 V sweep;
  Detector: 2,800 V; and
  Measuring equipment: Accu TOF JMS-T100LC (JEOL).
  (10): marker having a retention time of 2.26±0.5 (min) and an accurate mass (m/z) of 286.13±10 mDa in positive ion measurement $[M+H]^+$;
  (11): marker having a retention time of 8.29±0.5 (min) and an accurate mass (m/z) of 495.23±10 mDa in positive ion measurement $[M+H]^+$;
  (12): marker having a retention time of 8.32±0.5 (min) and an accurate mass (m/z) of 529.22±10 mDa in positive ion measurement $[M+H]^+$;
  (13): marker having a retention time of 8.64±0.5 (min) and an accurate mass (m/z) of 304.13±10 mDa in positive ion measurement $[M+H]^+$;
  (14): marker having a retention time of 9.24±0.5 (min) and an accurate mass (m/z) of 389.21±10 mDa in positive ion measurement $[M+H]^+$;
  (15): marker having a retention time of 3.93±0.5 (min) and an accurate mass (m/z) of 197.06±10 mDa in negative ion measurement $[M-H]^-$; and
  (16): marker having a retention time of 5.55±0.5 (min) and an accurate mass (m/z) of 327.09±10 mDa in negative ion measurement $[M-H]^-$; and (B-2) a means of determining that the stage of chronic kidney disease in the subject is severe when the at least one marker is detected by means (A-2).

Each of the devices (1) and (2) for determining the stage of chronic kidney disease according to the present invention includes a means of evaluating the marker content (means (A-1) or (A-2)), and a means of determining the stage of chronic kidney disease (means (B-1) and (C-1), or (B-2)). Hereinbelow, the means of the present invention are detailed.

Means of Evaluating the Marker Content

The means of evaluating the marker content is a means of evaluating the content of at least one marker selected from the group consisting of (1) to (16) or (10) to (16) in a specimen extracted from a human.

The means of evaluating the marker content is a means that performs the step of evaluating the marker content, which is explained in the method for determining the stage of chronic kidney disease of the present invention. The explanation regarding the means of evaluating the marker content is omitted because it is the same as the explanation regarding the step of evaluating the marker content.

Means of Determining the Stage of Chronic Kidney Disease

The means of determining the stage of chronic kidney disease is a means in which the marker content evaluated by means (A-1) is compared with the reference content range determined in each stage; when each marker content is within the reference content range of the same stage, the chronic kidney disease in the donor of the specimen is considered to be in that stage.

Means (B-2) is a means of determining that the stage of chronic kidney disease in the donor of the specimen is severe when the presence of at least one marker is confirmed by means (A-2).

Means (A-1) is a means of quantitatively evaluating the marker content. The reference content determined in the same manner as explained in the step of determining the stage of chronic kidney disease in the method of determining the stage of chronic kidney disease according to the present invention can be used.

The means of comparing the marker content evaluated by means (A-1) with the reference content range may be a means of comparing the marker content evaluated by means (A-1) with the reference content range stored in a memory.

The means of comparing the marker content evaluated by means (A-1) with the reference content range may be a means of allowing a person operating a device to compare the marker content and the reference content range. For example, the means may include a means of visual or aural transmission of the marker content evaluated by means (A-1) to a person operating the device. Examples of the means of visual transmission include a display that displays the marker content. Examples of the means of oral transmission include a sound emitter that audibly releases the marker content.

The means of determining the stage of chronic kidney disease may further include a means of demonstrating determination results. Although the means of demonstrating determination results is not limited, it may be a means of visually demonstrating the determination results in another display, a means of orally indicating the determination results, or a means of further transmitting the determination results to the outside.

Method for Operating the Device that Determines the Stage of Chronic Kidney Disease The method for operating device (1) that determines the stage of chronic kidney disease is a method comprising the steps of:

(a-1) operating means (A-1) to measure the content of at least one marker selected from the group consisting of markers (1) to (16) in a specimen extracted from a subject, (b-1) operating means (B-1) to determine a stage indicated by each marker by comparing the content measured in step (a-1) with a reference content range determined in each stage, and (c-1) operating means (C-1) to determine that when each marker indicates the same stage, which has been determined in step (b-1), the chronic kidney disease in the subject is in that stage.

The method for operating the device (2) that determines the stage of chronic kidney disease is a method comprising the steps of:

(a-2) operating means (A-2) to measure at least one marker selected from the group consisting of markers (10) to (16) in a specimen extracted from a subject, and (b-2) operating means (B-2) to determine that a stage of chronic kidney disease in the subject is severe when the at least one marker is detected in the specimen in step (a-2).

The explanation regarding specimens, markers, and steps for evaluating the marker content is omitted because it is the same as the explanation of the device for determining the stage of chronic kidney disease of the present invention.

III. Kit for Determining the Stage of Chronic Kidney Disease

The kit (1) for determining the stage of chronic kidney disease according to the present invention is a kit including a material required for detecting at least one marker selected from the group consisting of markers (1) to (16).

The kit (2) for determining the stage of chronic kidney disease according to the present invention is a kit including a material required for detecting at least one marker selected from the group consisting of markers (10) to (16).

The explanation of the marker is the same as that explained in the "method for determining the stage of chronic kidney disease" of the present invention.

The material required for detecting at least one marker selected from the group consisting of markers (1) to (16) is not limited, as long as it can detect the markers. Examples thereof include a material that specifically reacts with the markers. By reacting such a material with a specimen to detect the presence or absence of a reaction product, or the concentration of the reaction product, markers can be detected. Examples of the material that specifically reacts with the markers include enzymes specifically metabolizing the markers. For example, when hydrolase, which is used as an enzyme, is specifically reacted with markers to generate carbon dioxide ($CO_2$) and water ($H_2O$), thus decreasing the concentration of oxygen ($O_2$), the marker content can be quantitatively analyzed by detecting a decrease in the oxygen concentration using an oxygen electrode, and the like.

EXAMPLES

The present invention is described in further detail with reference to the Examples; however, the scope of the invention is not limited to these Examples. Markers that can be used as an index of the stage of chronic kidney disease were searched for using human blood specimens.

As specimens, plasma specimens were used. Specimens were extracted from 26 patients shown in Table 2. The staging shown in Table 2 is the same as that in Table 1.

TABLE 2

| Stage | Number of patients |
|---|---|
| Healthy person | 5 |
| 2 | 6 |
| 3 | 5 |
| 4 | 5 |
| 5 | 5 |

As a means of analysis, LC-TOF MS was used. The analysis was performed in the following manner. The plasma specimen or urine specimen was centrifuged for 15 minutes at 10,000 g, and precipitation was removed. The resultant was subjected to solid phase extraction using a solid phase column (Sep-Pak Light C18 Cartridge; Japanese Waters, Inc.) in accordance with the following procedure. The resultant was used as an evaluation sample to be subjected to LC-TOF MS.

Solid Phase Extraction Conditions

1. The solid phase column was conditioned with 1 mL of MetOH.
2. The solid phase column was equilibrated with 1 mL of ultra-pure water.
3. 500 μL of a plasma specimen was loaded to the solid phase column.
4. Washing was performed with 2 mL of ultra-pure water.
5. Elution was performed with 300 μL of 90% MetOH.
6. As internal standard substances, benzyloxycarbonyl-L-tyrosyl-glutamic acid (Z-Tyr-Glu) and tosyl-L-arginine methyl ester monohydrochloride (Tos-Arg-OMe-HCl) were added to the eluted sample.

The sample measured was subjected to LC-TOF MS. Liquid chromatography (LC) was performed under either of the following conditions (n=3).

Condition 1

LC Conditions
LC equipment: Agilent 1100 Series (Agilent)
Column: Cadenza C18 2×150 mm, 3 μm (Imtakt)
Pre-column: TCI OPTI-GUARD Fit ODS (TCI)
Mobile phase A: 0.05% formic acid
Mobile phase B: acetonitrile
For gradient elution:
0 to 15 min: linear gradient from 5% to 95% mobile phase B in mobile phase A,
15 to 20 min: linear gradient from 95% to 100% mobile phase B in mobile phase A, and
20 to 35 min: 100% mobile phase B is kept;
Flow rate: 0.2 mL/min; and
Measurement sample content: 5 μL.

The conditions of the time of flight mass spectrometry (TOF MS) were as follows.
TOF MS Conditions
Measuring range: m/z 70 to 1,000;
Orifice 1 voltage: 10 to 40V, −10 to (−40) V sweep;
Ion guide voltage: 500 to 2,500 V sweep;
Detector: 2,800 V; and
Measuring equipment: Accu TOF JMS-T100LC (JEOL).

Two kinds of amino acid derivatives are mixed as internal standard substances with the plasma specimen, and analysis was performed. The value obtained by dividing the peak area of $[M+H]^+$ (ESI Positive) ion or $[M-H]^-$ (ESI Negative) ion by the average peak area of internal standard substances was compared as a relative area. Table 3 shows the retaining time and the accurate mass of candidates for markers.

TABLE 3

| Peak No. | Retention time (min) | m/z | Accurate mass Tos(342) | Z(444) |
|---|---|---|---|---|
| ESI-Positive (18) 21 Components ||||| 
| Posi-No. 14 | 2.03 | 104.11 | 104.10345 | 104.10371 |
| Posi-No. 16 | 2.26 | 286.12 | 286.13367 | 286.13436 |
| Posi-No. 22 | 3.70 | 229.16 | 229.14824 | 229.1488 |
| Posi-No. 23 | 3.80 | 257.12 | 257.10263 | 257.10325 |
| Posi-No. 31 | 5.43 | 283.15 | 283.098 | 283.09868 |
| Posi-No. 44 | 6.52 | 312.15 | 312.12285 | 312.1236 |
| Posi-No. 54 | 6.87 | 232.17 | 232.15157 | 232.15213 |
| Posi-No. 80 | 8.29 | 231.13 | 231.11092 | 231.11148 |
| Posi-No. 82 | 8.29 | 495.26 | 495.22883 | 495.23003 |
| Posi-No. 86 | 8.32 | 265.13 | 265.11507 | 265.11571 |
| Posi-No. 88 | 8.32 | 529.28 | 529.2246 | 529.22587 |
| Posi-No. 96 | 8.51 | 180.08 | 180.06427 | 180.0647 |
| Posi-No. 97 | 8.64 | 304.15 | 304.13009 | 304.13082 |
| Posi-No. 113 | 9.24 | 389.24 | 389.21338 | 389.21432 |
| Posi-No. 118 | 9.36 | 527.32 | 527.28428 | 527.28556 |
| Posi-No. 135 | 9.87 | 447.25 | 447.24668 | 447.22307 |
| Posi-No. 142 | 9.91 | 541.36 | 541.31245 | 541.31375 |
| Posi-No. 184 | 10.54 | 300.23 | 300.21515 | 300.21588 |
| ESI Negative (6) ||||| 
| Nega-No. 18 | 3.93 | 197.14 | 197.05604 | 197.05597 |
| Nega-No. 21 | 5.55 | 327.28 | 327.08651 | 327.08639 |
| Nega-No. 27 | 6.57 | 211.17 | 211.07786 | 211.07778 |
| Nega-No. 33 | 7.19 | 411.31 | 411.1303 | 411.13015 |
| Nega-No. 49 | 8.25 | 263.22 | 263.10095 | 263.10086 |
| Nega-No. 53 | 8.32 | 309.24 | 309.10863 | 309.10852 |

Figure 2:
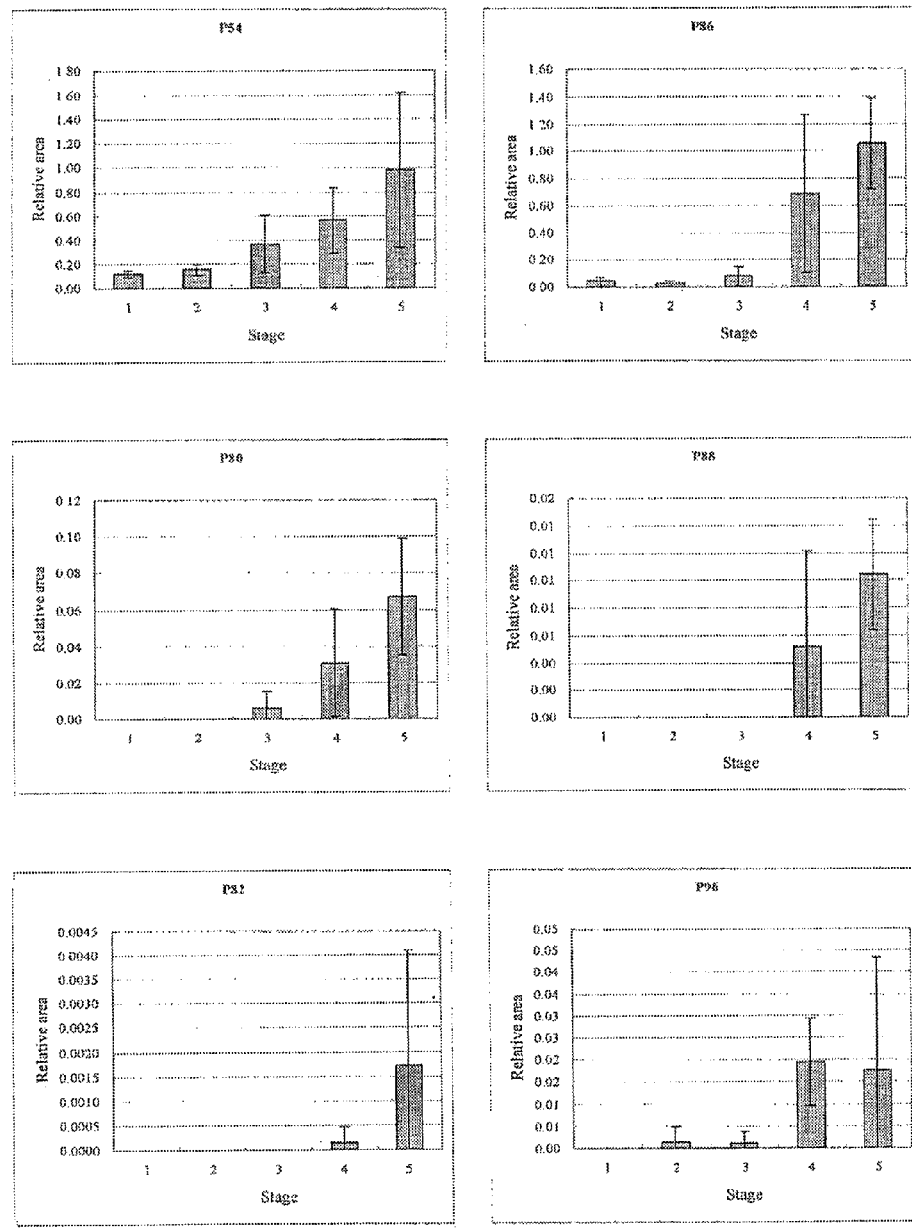
FIG. 2 shows graphs demonstrating the component change (SN>20) of each marker (ESI-Positive) in each stage.
Figure 3:
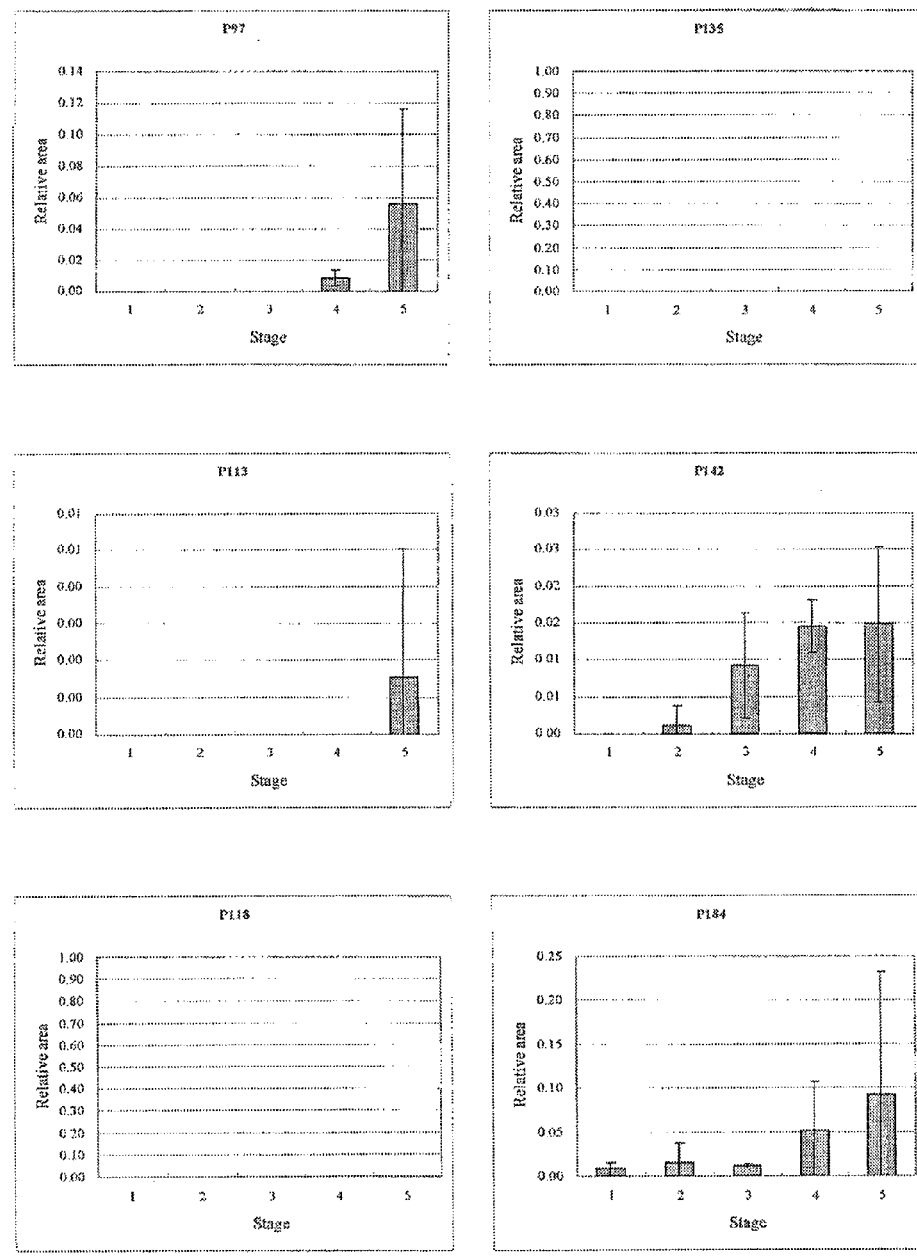
FIG. 3 shows graphs demonstrating the component change (SN>20) of each marker (ESI-Positive) in each stage.
Figure 4:
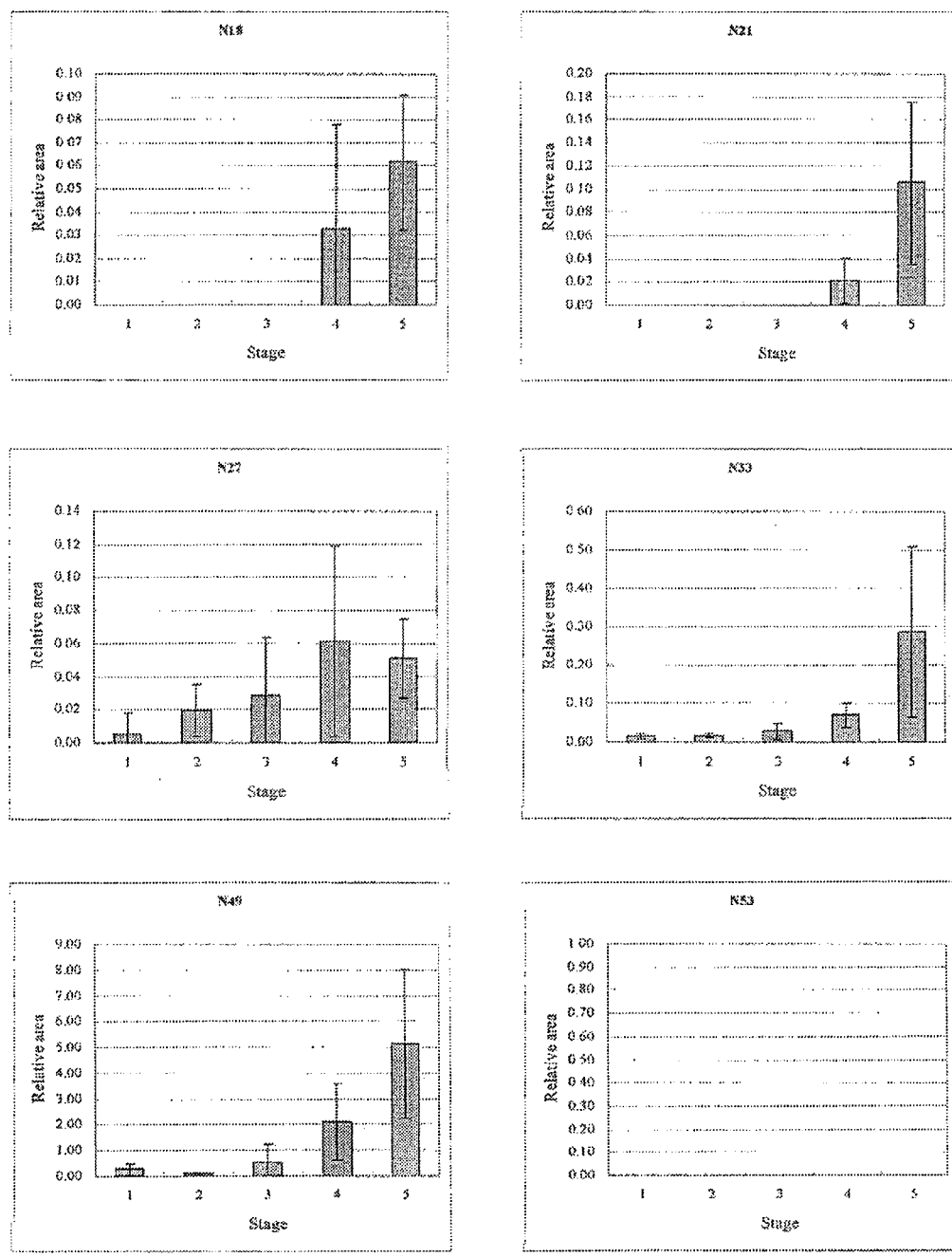
FIG. 4 shows graphs demonstrating the component change (SN>20) of each marker (ESI-Negative) in each stage.
Figure 5:
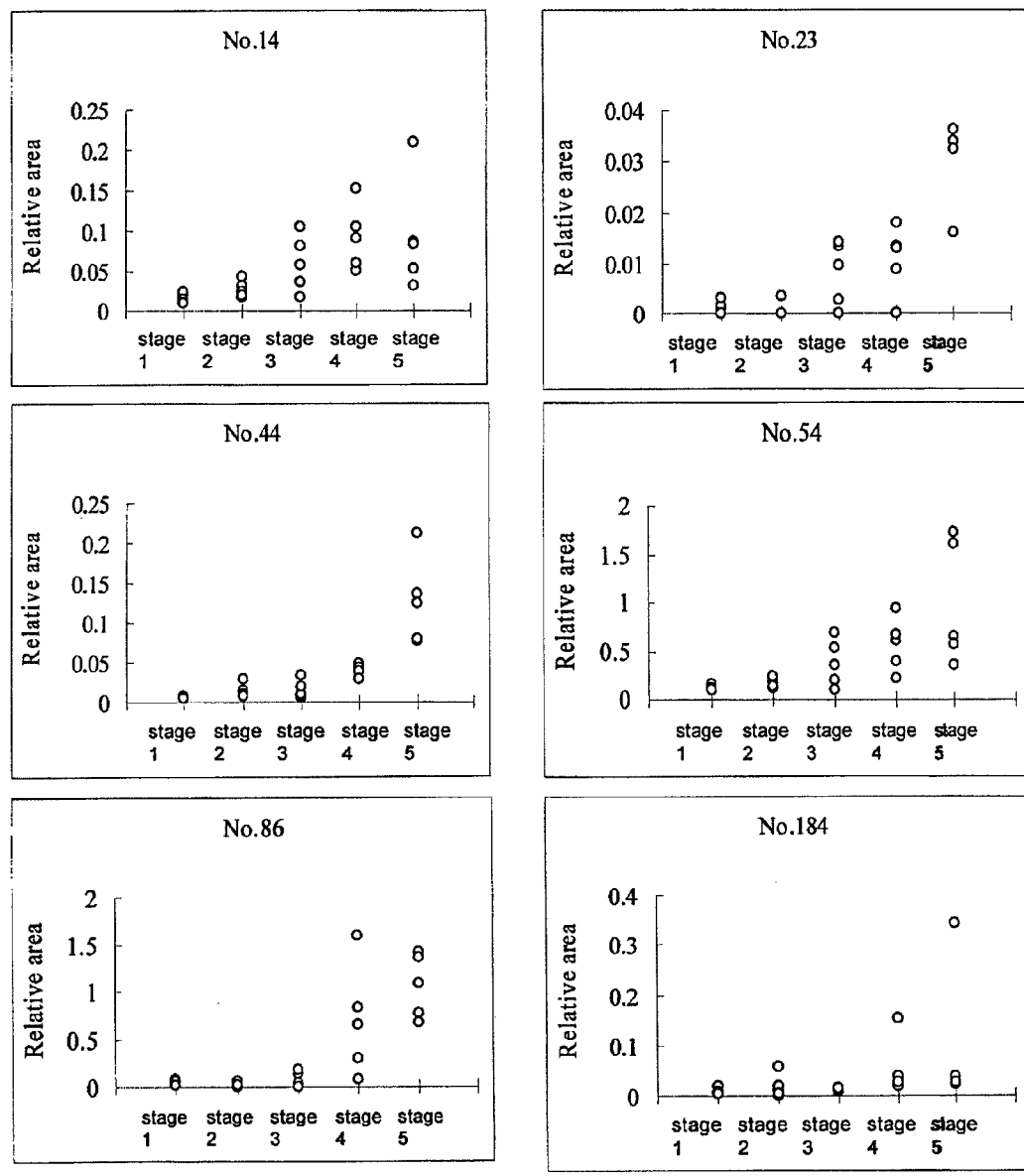
FIG. 5 shows graphs demonstrating the component change of each marker (ESI-Positive) in each stage.
Figure 6:
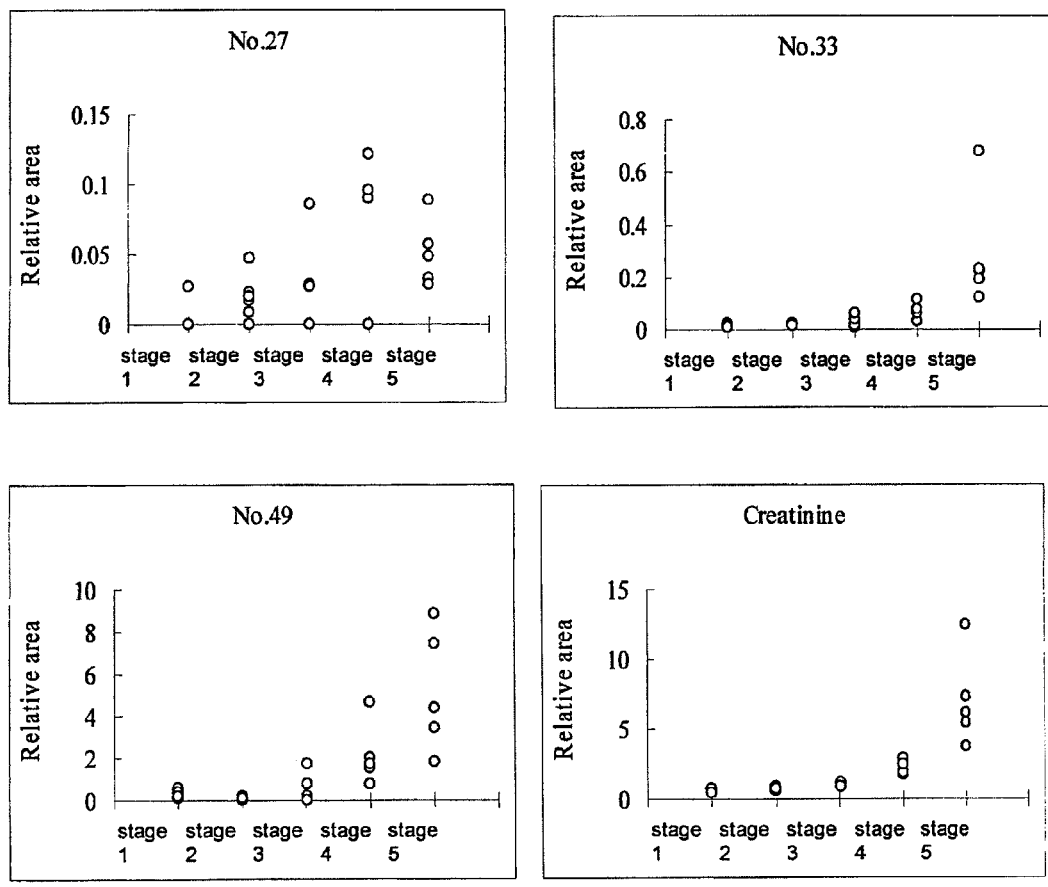
FIG. 6 shows graphs demonstrating the component change of each marker (ESI-Negative) in each stage.

Change of each marker in each stage was shown in FIGS. 1 to 6.

Consequently, regarding markers (1) to (9) (P-Nos. 14, 23, 44, 54, 86, and 184; and N-Nos. 27, 33, and 49, in this order), a tendency to increase the relative area was observed as the stage level was increased. Regarding markers (1) to (9), the degree of increase in the marker content was examined based on a healthy person (Tables 4 and 5).

TABLE 4

| | P-No. 14 | P-No. 23 | P-No. 44 | P-No. 54 | P-No. 86 | P-No. 184 | Creatinine (mg/dL) |
|---|---|---|---|---|---|---|---|
| Healthy person | 1.00 | 1.00 | 1.00 | 1.00 | 1.00 | 1.00 | 1.00 |
| Stage 2 | 1.52 | 0.54 | 2.43 | 1.30 | 0.56 | 1.95 | 1.12 |
| Stage 3 | 3.60 | 7.20 | 2.81 | 3.10 | 1.80 | 1.49 | 1.62 |
| Stage 4 | 5.59 | 9.62 | 7.55 | 4.74 | 16.30 | 6.47 | 3.29 |
| Stage 5 | 5.60 | 24.19 | 24.10 | 8.24 | 24.97 | 11.78 | 10.73 |

TABLE 5

| | N-No. 27 | N-No. 33 | N-No. 49 | Creatinine (mg/dL) |
|---|---|---|---|---|
| Healthy person | 1.00 | 1.00 | 1.00 | 1.00 |
| Stage 2 | 3.56 | 1.08 | 0.31 | 1.12 |
| Stage 3 | 5.19 | 1.76 | 1.99 | 1.62 |
| Stage 4 | 11.28 | 4.42 | 7.74 | 3.29 |
| Stage 5 | 9.37 | 18.12 | 18.85 | 10.73 |

Regarding markers (10) to (16) (P-Nos. 16, 82, 88, 97, and 113; and N-Nos. 18 and 21, in this order), the relative area could not be confirmed in a healthy person, and in persons in stages 2 and 3; however, a tendency to increase the relative area was observed in stages 4 and 5. In particular, the relative area of marker (14) (P-No. 113) could not be confirmed in a healthy person, and in persons in stages 2 to 4; however, a tendency to increase the relative area was observed in stage 5.

The results indicate that the stage of chronic kidney disease can be predicted by measuring markers (1) to (16). In particular, the results indicate that chronic kidney disease in an earlier stage can be discovered by measuring markers (1) to (9). The results also indicate that patients in which markers (10) to (16) were measured in their specimens can be predicted to be in stage 4 or 5; and particularly, that patients in which marker (14) was measured in their specimens can be predicted to be in stage 5.

The invention claimed is:

1. A method for determining a stage of chronic kidney disease in a subject suffering from kidney disease, the method comprising the steps of:

(A-1) measuring the content of at least one marker selected from the group consisting of markers (1) to (16) shown below by subjecting a specimen from the subject using liquid chromatography/time of flight mass spectrometry under the following conditions:

Liquid-Chromatography Conditions
Liquid-chromatography equipment: Agilent 1100 Series (Agilent);
Column: Cadenza C18 2×150 mm, 3 μm (Imtakt);
Pre-column: TCI OPTI-GUARD Fit ODS (TCI);
Mobile phase A: 0.05% formic acid;
Mobile phase B: acetonitrile;
For gradient elution:
0 to 15 min: linear gradient from 5% to 95% mobile phase B in mobile phase A,
15 to 20 min: linear gradient from 95% to 100% mobile phase B in mobile phase A, and
20 to 35 min: 100% mobile phase B is kept;
Flow rate: 0.2 mL/min; and
Measurement sample content: 5 μL.
Time of Flight Mass Spectrometry Conditions
Measuring range: m/z 70 to 1,000;
Orifice 1 voltage: 10 to 40V, −10 to (−40) V sweep;
Ion guide voltage: 500 to 2,500 V sweep;
Detector: 2,800 V; and
Measuring equipment: Accu TOF JMS-T100LC (JEOL).
Markers
(1): marker having a retention time of 2.03±0.5 (min) and an accurate mass (m/z) of 104.10±10 mDa in positive ion measurement $[M+H]^+$;
(2): marker having a retention time of 3.80±0.5 (min) and an accurate mass (m/z) of 257.10±10 mDa in positive ion measurement $[M+H]^+$;
(3): marker having a retention time of 6.52±0.5 (min) and an accurate mass (m/z) of 312.12±10 mDa in positive ion measurement $[M+H]^+$;
(4): marker having a retention time of 6.87±0.5 (min) and an accurate mass (m/z) of 232.15±10 mDa in positive ion measurement $[M+H]^+$;
(5): marker having a retention time of 8.32±0.5 (min) and an accurate mass (m/z) of 265.12±10 mDa in positive ion measurement $[M+H]^+$;
(6): marker having a retention time of 10.54±0.5 (min) and an accurate mass (m/z) of 300.22±10 mDa in positive ion measurement $[M+H]^+$;
(7): marker having a retention time of 6.57±0.5 (min) and an accurate mass (m/z) of 211.08±10 mDa in negative ion measurement $[M-H]^-$;
(8): marker having a retention time of 7.19±0.5 (min) and an accurate mass (m/z) of 411.13±10 mDa in negative ion measurement $[M-H]^-$;
(9): marker having a retention time of 8.25±0.5 (min) and an accurate mass (m/z) of 263.10±10 mDa in negative ion measurement $[M-H]^-$;
(10): marker having a retention time of 2.26±0.5 (min) and an accurate mass (m/z) of 286.13±10 mDa in positive ion measurement $[M+H]^+$;
(11): marker having a retention time of 8.29±0.5 (min) and an accurate mass (m/z) of 495.23±10 mDa in positive ion measurement $[M+H]^+$;
(12): marker having a retention time of 8.32±0.5 (min) and an accurate mass (m/z) of 529.22±10 mDa in positive ion measurement $[M+H]^+$;
(13): marker having a retention time of 8.64±0.5 (min) and an accurate mass (m/z) of 304.13±10 mDa in positive ion measurement $[M+H]^+$;
(14): marker having a retention time of 9.24±0.5 (min) and an accurate mass (m/z) of 389.21±10 mDa in positive ion measurement $[M+H]^+$;
(15): marker having a retention time of 3.93±0.5 (min) and an accurate mass (m/z) of 197.05±10 mDa in negative ion measurement $[M-H]^-$; and
(16): marker having a retention time of 5.55±0.5 (min) and an accurate mass (m/z) of 327.09±10 mDa in negative ion measurement $[M-H]^-$, (B-1) determining the stage indicated by each marker by comparing the content of each marker in the specimen from the subject, which has been measured in step (A-1), with a reference content range determined in each stage; and (C-1) determining that when each marker indicates the same stage, which has been determined in step (B-1), the chronic kidney disease in the subject is in that stage.

2. The method according to claim 1, wherein the marker measured in step (A-1) is at least one marker selected from the group consisting of markers (1) to (9).

3. A method for determining a stage of chronic kidney disease in a subject suffering from kidney disease, comprising the steps of:

(B-1) determining the stage indicated by each marker by comparing the content of at least one marker selected from the group consisting of markers (1) to (16) shown below, which has been measured by subjecting a specimen from the subject using liquid chromatography/time of flight mass spectrometry under the following conditions, with a reference content range determined in each stage, Liquid-Chromatography Conditions
Liquid-chromatography equipment: Agilent 1100 Series (Agilent);
Column: Cadenza C18 2×150 mm, 3 μm (Imtakt);
Pre-column: TCI OPTI-GUARD Fit ODS (TCI);
Mobile phase A: 0.05% formic acid;
Mobile phase B: acetonitrile;
For gradient elution:
0 to 15 min: linear gradient from 5% to 95% mobile phase B in mobile phase A,
15 to 20 min: linear gradient from 95% to 100% mobile phase B in mobile phase A, and
20 to 35 min: 100% mobile phase B is kept;
Flow rate: 0.2 mL/min; and
Measurement sample content: 5 μL.
Time of Flight Mass Spectrometry Conditions
Measuring range: m/z 70 to 1,000;
Orifice 1 voltage: 10 to 40V, −10 to (−40) V sweep;
Ion guide voltage: 500 to 2,500 V sweep;
Detector: 2,800 V; and
Measuring equipment: Accu TOF 3MS-T100LC (JEOL).

Markers (1): marker having a retention time of 2.03±0.5 (min) and an accurate mass (m/z) of 104.10±10 mDa in positive ion measurement [M+H]$^+$;

(2): marker having a retention time of 3.80±0.5 (min) and an accurate mass (m/z) of 257.10±10 mDa in positive ion measurement [M+H]$^+$;

(3): marker having a retention time of 6.52±0.5 (min) and an accurate mass (m/z) of 312.12±10 mDa in positive ion measurement [M+H]$^+$;

(4): marker having a retention time of 6.87±0.5 (min) and an accurate mass (m/z) of 232.15±10 mDa in positive ion measurement [M+H]$^+$;

(5): marker having a retention time of 8.32±0.5 (min) and an accurate mass (m/z) of 265.12±10 mDa in positive ion measurement [M+H]$^+$;

(6): marker having a retention time of 10.54±0.5 (min) and an accurate mass (m/z) of 300.22±10 mDa in positive ion measurement [M+H]$^+$;

(7): marker having a retention time of 6.57±0.5 (min) and an accurate mass (m/z) of 211.08±10 mDa in negative ion measurement [M−H]$^+$;

(8): marker having a retention time of 7.19±0.5 (min) and an accurate mass (m/z) of 411.13±10 mDa in negative ion measurement [M−H]$^-$;

(9): marker having a retention time of 8.25±0.5 (min) and an accurate mass (m/z) of 263.10±10 mDa in negative ion measurement [M−H]$^-$;

(10): marker having a retention time of 2.26±0.5 (min) and an accurate mass (m/z) of 286.13±10 mDa in positive ion measurement [M+H]$^+$;

(11): marker having a retention time of 8.29±0.5 (min) and an accurate mass (m/z) of 495.23±10 mDa in positive ion measurement [M+H]$^+$;

(12): marker having a retention time of 8.32±0.5 (min) and an accurate mass (m/z) of 529.22±10 mDa in positive ion measurement [M+H]$^+$;

(13): marker having a retention time of 8.64±0.5 (min) and an accurate mass (m/z) of 304.13±10 mDa in positive ion measurement [M+H]$^+$;

(14): marker having a retention time of 9.24±0.5 (min) and an accurate mass (m/z) of 389.21±10 mDa in positive ion measurement [M+H]$^+$;

(15): marker having a retention time of 3.93±0.5 (min) and an accurate mass (m/z) of 197.05±10 mDa in negative ion measurement [M−H]$^-$; and (16): marker having a retention time of 5.55±0.5 (min) and an accurate mass (m/z) of 327.09±10 mDa in negative ion measurement [M−H]$^-$, and (C-1) determining that when each marker indicates the same stage, which has been determined in step (B-1), the chronic kidney disease in the subject is in that stage.

4. The method according to claim 3, wherein the marker of interest in step (B-1) is at least one marker selected from the group consisting of markers (1) to (9).

5. A method for determining a stage of chronic kidney disease in a subject suffering from kidney disease, the method comprising the steps of:

(A-2) measuring the presence of at least one marker selected from the group consisting of markers (10) to (16) shown below by subjecting a specimen from the subject using liquid chromatography/time of flight mass spectrometry under the following conditions:

Liquid-Chromatography Conditions

Liquid-chromatography equipment: Agilent 1100 Series (Agilent);

Column: Cadenza C18 2×150 mm, 3 μm (Imtakt);

Pre-column: TCI OPTI-GUARD Fit ODS (TCI);

Mobile phase A: 0.05% formic acid;

Mobile phase B: acetonitrile;

For gradient elution:

0 to 15 min: linear gradient from 5% to 95% mobile phase B in mobile phase A, 15 to 20 min: linear gradient from 95% to 100% mobile phase B in mobile phase A, and 20 to 35 min: 100% mobile phase B is kept;

Flow rate: 0.2 mL/min; and

Measurement sample content: 5 μL.

Time of Flight Mass Spectrometry Conditions

Measuring range: m/z 70 to 1,000;

Orifice 1 voltage: 10 to 40V, −10 to (−40) V sweep;

Ion guide voltage: 500 to 2,500 V sweep;

Detector: 2,800 V; and

Measuring equipment: Accu TOF JMS-T100LC (JEOL).

Markers (10): marker having a retention time of 2.26±0.5 (min) and an accurate mass (m/z) of 286.13±10 mDa in positive ion measurement [M+H]$^+$;

(11): marker having a retention time of 8.29±0.5 (min) and an accurate mass (m/z) of 495.26±10 mDa in positive ion measurement [M+H]$^+$;

(12): marker having a retention time of 8.32±0.5 (min) and an accurate mass (m/z) of 529.28±10 mDa in positive ion measurement [M+H]$^+$;

(13): marker having a retention time of 8.64±0.5 (min) and an accurate mass (m/z) of 304.15±10 mDa in positive ion measurement [M+H]$^+$;

(14): marker having a retention time of 9.24±0.5 (min) and an accurate mass (m/z) of 389.24±10 mDa in positive ion measurement [M+H]$^+$;

(15): marker having a retention time of 3.93±0.5 (min) and an accurate mass (m/z) of 197.14±10 mDa in negative ion measurement [M−H]$^-$; and (16): marker having a retention time of 5.55±0.5 (min) and an accurate mass (m/z) of 327.28±10 mDa in negative ion measurement [M−H]$^-$, and (B-2) determining that the stage of chronic kidney disease in the subject is severe when the at least one marker is detected in step (A-2).

6. A device for determining a stage of chronic kidney disease in a subject suffering from kidney disease, the device comprising:

(A-1) a means of measuring the content of at least one marker selected from the group consisting of markers (1) to (16) shown below in a specimen from the subject using liquid chromatography/time of flight mass spectrometry under the following conditions:

Liquid-Chromatography Conditions

Liquid-chromatography equipment: Agilent 1100 Series (Agilent);

Column: Cadenza C18 2×150 mm, 3 μm (Imtakt);

Pre-column: TCI OPTI-GUARD Fit ODS (TCI);

Mobile phase A: 0.05% formic acid;

Mobile phase B: acetonitrile;

For gradient elution:

0 to 15 min: linear gradient from 5% to 95% mobile phase B in mobile phase A, 15 to 20 min: linear gradient from 95% to 100% mobile phase B in mobile phase A, and 20 to 35 min: 100% mobile phase B is kept;

Flow rate: 0.2 mL/min; and

Measurement sample content: 5 μL.

Time of Flight Mass Spectrometry Conditions

Measuring range: m/z 70 to 1,000;

Orifice 1 voltage: 10 to 40V, −10 to (−40) V sweep;
Ion guide voltage: 500 to 2,500 V sweep;
Detector: 2,800 V; and
Measuring equipment: Accu TOF JMS-T100LC (JEOL).
Markers
(1): marker having a retention time of 2.03±0.5 (min) and an accurate mass (m/z) of 104.10±10 mDa in positive ion measurement [M+H]$^+$;
(2): marker having a retention time of 3.80±0.5 (min) and an accurate mass (m/z) of 257.10±10 mDa in positive ion measurement [M+H]$^+$;
(3): marker having a retention time of 6.52±0.5 (min) and an accurate mass (m/z) of 312.12±10 mDa in positive ion measurement [M+H]$^+$;
(4): marker having a retention time of 6.87±0.5 (min) and an accurate mass (m/z) of 232.15±10 mDa in positive ion measurement [M+H]$^+$;
(5): marker having a retention time of 8.32±0.5 (min) and an accurate mass (m/z) of 265.12±10 mDa in positive ion measurement [M+H]$^+$;
(6): marker having a retention time of 10.54±0.5 (min) and an accurate mass (m/z) of 300.22±10 mDa in positive ion measurement [M+H]$^+$;
(7): marker having a retention time of 6.57±0.5 (min) and an accurate mass (m/z) of 211.10±10 mDa in negative ion measurement [M−H]$^−$;
(8): marker having a retention time of 7.19±0.5 (min) and an accurate mass (m/z) of 411.13±10 mDa in negative ion measurement [M−H]$^−$;
(9): marker having a retention time of 8.25±0.5 (min) and an accurate mass (m/z) of 263.10±10 mDa in negative ion measurement [M−H]$^−$;
(10): marker having a retention time of 2.26±0.5 (min) and an accurate mass (m/z) of 286.13±10 mDa in positive ion measurement [M+H]$^+$;
(11): marker having a retention time of 8.29±0.5 (min) and an accurate mass (m/z) of 495.23±10 mDa in positive ion measurement [M+H]$^+$;
(12): marker having a retention time of 8.32±0.5 (min) and an accurate mass (m/z) of 529.22±10 mDa in positive ion measurement [M+H]$^+$;
(13): marker having a retention time of 8.64±0.5 (min) and an accurate mass (m/z) of 304.13±10 mDa in positive ion measurement [M+H]$^+$;
(14): marker having a retention time of 9.24±0.5 (min) and an accurate mass (m/z) of 389.21±10 mDa in positive ion measurement [M+H]$^+$;
(15): marker having a retention time of 3.93±0.5 (min) and an accurate mass (m/z) of 197.05±10 mDa in negative ion measurement [M−H]$^−$; and
(16): marker having a retention time of 5.55±0.5 (min) and an accurate mass (m/z) of 327.09±10 mDa in negative ion measurement [M−H]$^−$,
(B-1) a means of determining the stage indicated by each marker by comparing the content of each marker in the specimen from the subject, which has been measured by means (A-1), with a reference content range determined in each stage, and
(C-1) a means of determining that when each marker indicates the same stage, which has been determined by means (B-1), the chronic kidney disease in the subject is in that stage.

7. The device according to claim 6, wherein the marker measured by means (A-1) is at least one marker selected from the group consisting of markers (1) to (9).

8. A device for determining a stage of chronic kidney disease in a subject suffering from kidney disease, the device comprising:
(A-2) a means of measuring at least one marker selected from the group consisting of markers (10) to (16) shown below using liquid chromatography/time of flight mass spectrometry under the following conditions:
Liquid-Chromatography Conditions
Liquid-chromatography equipment: Agilent 1100 Series (Agilent);
Column: Cadenza C18 2×150 mm, 3 μm (Imtakt);
Pre-column: TCI OPTI-GUARD Fit ODS (TCI);
Mobile phase A: 0.05% formic acid;
Mobile phase B: acetonitrile;
For gradient elution:
0 to 15 min: linear gradient from 5% to 95% mobile phase B in mobile phase A,
15 to 20 min: linear gradient from 95% to 100% mobile phase B in mobile phase A, and
20 to 35 min: 100% mobile phase B is kept;
Flow rate: 0.2 mL/min; and
Measurement sample content: 5 μL.
Time of Flight Mass Spectrometry Conditions
Measuring range: m/z 70 to 1,000;
Orifice 1 voltage: 10 to 40V, −10 to (−40) V sweep;
Ion guide voltage: 500 to 2,500 V sweep;
Detector: 2,800 V; and
Measuring equipment: Accu TOF JMS-T100LC (JEOL).
Markers
(10): marker having a retention time of 2.26±0.5 (min) and an accurate mass (m/z) of 286.13±10 mDa in positive ion measurement [M+H]$^+$;
(11): marker having a retention time of 8.29±0.5 (min) and an accurate mass (m/z) of 495.23±10 mDa in positive ion measurement [M+H]$^+$;
(12): marker having a retention time of 8.32±0.5 (min) and an accurate mass (m/z) of 529.22±10 mDa in positive ion measurement [M+H]$^+$;
(13): marker having a retention time of 8.64±0.5 (min) and an accurate mass (m/z) of 304.13±10 mDa in positive ion measurement [M+H]$^+$;
(14): marker having a retention time of 9.24±0.5 (min) and an accurate mass (m/z) of 389.21±10 mDa in positive ion measurement [M+H]$^+$;
(15): marker having a retention time of 3.93±0.5 (min) and an accurate mass (m/z) of 197.06±10 mDa in negative ion measurement [M−H]$^−$; and
(16): marker having a retention time of 5.55±0.5 (min) and an accurate mass (m/z) of 327.09±10 mDa in negative ion measurement [M−H]$^−$, and
(B-2) a means of determining that the stage of chronic kidney disease in the subject is severe when the at least one marker is detected in step (A-2).

9. A kit for determining a stage of chronic kidney disease comprising a material required for detecting at least one marker selected from the group consisting of markers (1) to (16) shown below using liquid chromatography/time of flight mass spectrometry under the following conditions:
Liquid-Chromatography Conditions
Liquid-chromatography equipment: Agilent 1100 Series (Agilent);
Column: Cadenza C18 2×150 mm, 3 μm (Imtakt);
Pre-column: TCI OPTI-GUARD Fit ODS (TCI);
Mobile phase A: 0.05% formic acid;
Mobile phase B: acetonitrile;

For gradient elution:
0 to 15 min: linear gradient from 5% to 95% mobile phase B in mobile phase A,
15 to 20 min: linear gradient from 95% to 100% mobile phase B in mobile phase A, and
20 to 35 min: 100% mobile phase B is kept;
Flow rate: 0.2 mL/min; and
Measurement sample content: 5 μL.
Time of Flight Mass Spectrometry Conditions
Measuring range: m/z 70 to 1,000;
Orifice 1 voltage: 10 to 40V, −10 to (−40) V sweep;
Ion guide voltage: 500 to 2,500 V sweep;
Detector: 2,800 V; and
Measuring equipment: Accu TOF JMS-T100LC (JEOL).
Markers (1): marker having a retention time of 2.03±0.5 (min) and an accurate mass (m/z) of 104.10±10 mDa in positive ion measurement $[M+H]^+$;

(2): marker having a retention time of 3.80±0.5 (min) and an accurate mass (m/z) of 257.10±10 mDa in positive ion measurement $[M+H]^+$;

(3): marker having a retention time of 6.52±0.5 (min) and an accurate mass (m/z) of 312.12±10 mDa in positive ion measurement $[M+H]^+$;

(4): marker having a retention time of 6.87±0.5 (min) and an accurate mass (m/z) of 232.15±10 mDa in positive ion measurement $[M+H]^+$;

(5): marker having a retention time of 8.32±0.5 (min) and an accurate mass (m/z) of 265.12±10 mDa in positive ion measurement $[M+H]^+$;

(6): marker having a retention time of 10.54±0.5 (min) and an accurate mass (m/z) of 300.22±10 mDa in positive ion measurement $[M+H]^+$;

(7): marker having a retention time of 6.57±0.5 (min) and an accurate mass (m/z) of 211.10±10 mDa in negative ion measurement $[M-H]^-$;

(8): marker having a retention time of 7.19±0.5 (min) and an accurate mass (m/z) of 411.13±10 mDa in negative ion measurement $[M-H]^-$;

(9): marker having a retention time of 8.25±0.5 (min) and an accurate mass (m/z) of 263.10±10 mDa in negative ion measurement $[M-H]^-$;

(10): marker having a retention time of 2.26±0.5 (min) and an accurate mass (m/z) of 286.13±10 mDa in positive ion measurement $[M+H]^+$;

(11): marker having a retention time of 8.29±0.5 (min) and an accurate mass (m/z) of 495.23±10 mDa in positive ion measurement $[M+H]^+$;

(12): marker having a retention time of 8.32±0.5 (min) and an accurate mass (m/z) of 529.22±10 mDa in positive ion measurement $[M+H]^+$;

(13): marker having a retention time of 8.64±0.5 (min) and an accurate mass (m/z) of 304.13±10 mDa in positive ion measurement $[M+H]^+$;

(14): marker having a retention time of 9.24±0.5 (min) and an accurate mass (m/z) of 389.21±10 mDa in positive ion measurement $[M+H]^+$;

(15): marker having a retention time of 3.93±0.5 (min) and an accurate mass (m/z) of 197.05±10 mDa in negative ion measurement $[M-H]^-$; and (16): marker having a retention time of 5.55±0.5 (min) and an accurate mass (m/z) of 327.09±10 mDa in negative ion measurement $[M-H]^-$.

10. The kit according to claim 9, wherein the marker is at least one marker selected from the group consisting of markers (1) to (9).

11. The kit according to claim 9, wherein the marker is at least one marker selected from the group consisting of markers (10) to (16).

* * * * *